United States Patent [19]
Slimak

[11] Patent Number: 6,099,866
[45] Date of Patent: Aug. 8, 2000

[54] COMPOSITIONS FOR TOPICAL APPLICATION AND OTHER PRODUCTS FROM FRESH BEESWAXES

[76] Inventor: K. M. Slimak, P.O. Box 2444, Springfield, Va. 22152

[21] Appl. No.: 07/918,891

[22] Filed: Jul. 24, 1992

Related U.S. Application Data

[63] Continuation of application No. 07/683,343, Apr. 10, 1991, abandoned, which is a continuation-in-part of application No. 07/289,036, Dec. 23, 1988, abandoned, which is a continuation-in-part of application No. 07/427,987, Oct. 27, 1989, abandoned, which is a continuation of application No. 07/134,861, Dec. 18, 1987, abandoned, which is a continuation-in-part of application No. 06/825,657, Jan. 31, 1986, Pat. No. 4,793,991.

[51] Int. Cl.[7] .................................................. A61K 35/12
[52] U.S. Cl. ............................................................ 424/520
[58] Field of Search ....................................... 424/95, 520

[56] References Cited

PUBLICATIONS

Chem Abst. 101: 177251 n (1984).
Chem Abst. 68 : 9854 t (1968).

*Primary Examiner*—Zohreh Fay
*Attorney, Agent, or Firm*—Stevens, Davis, Miller & Mosher, L.L.P.

[57] ABSTRACT

The present invention is concerned with novel compositions containing fresh or virgin beeswaxes and oil, with and without water, and the utilization of such compositions for the treatment of skin in animals including man, for treatment for first, second, and third degree (partial and full thickness) burns due to sunburn, windburn, scalds, flash flame, electrical contact, chemical contact, cold, and the like, for use as a preventive aid for sunburn, windburns, skin chapping, chafing and the like, for promoting and accelerating the healing of burns, abrasions, lacerations, cuts, scratches, dry skin, chapped skin, wind burned skin, friction-type burns, chafing and the like, for use as a softening and moisturizing agent, for use in the reduction of wrinkles, for use as a topical application to irritations of the skin, including dry lips, chapped skin, abrasions, and the like, for use as an analgesic to be applied topically for the treatment and alleviation of pain in the skin and underlying tissues, for use as a protective barrier between the skin and other irritants, eg, saliva, urine, fecal material, various chemical irritants and the like, and for use as a base to which may be added other agents also promoting treatment, moisturization, protective or preventive measures for the skin.

24 Claims, No Drawings

COMPOSITIONS FOR TOPICAL APPLICATION AND OTHER PRODUCTS FROM FRESH BEESWAXES

RELATED APPLICATIONS

This application is a continuation of application Ser. No. 07/683,343, filed Apr. 10, 1991, now abandoned; which is a Continuation In Part of patent application Ser. No. 07/289,036 filed on Dec. 23, 1988; and as a Continuation in Part of patent application Ser. No. 07/427,987 filed on Oct. 27, 1989, which in turn is a continuation of patent application Ser. No. 07/134,861 filed on Dec. 18, 1987, now abandoned; is a Continuation In Part of patent application Ser. No. 06/825,657 filed on Jan. 31, 1986, now U.S. Pat. No. 4,793,991, the entire disclosures of each of which are herein incorporated by reference.

In my previous application Ser. No. 06/825,657, I disclosed the following: the utilization of beeswax from single plant sources as an ingredient in lip balms, lip sticks, and other cosmetic preparations. I have discovered that the single plant source beeswax and oil combinations were significantly softer and more pliable in consistency, than oil and prior Art beeswax combinations.

I have now found that the preferred range for beeswax and oil combinations ranges from 1:1 to 1:3, parts oil to parts water, by volume. The selection of the specific combination of oil and water will depend on the degree of pliability desired, the rate of mixing or whipping during cooling of the wax/oil solutions, the specific type of single plant source beeswax, and the length of time the wax is stored before use. For example, a single plant source beeswax which has been stored for a year or more, even at temperatures below freezing, will generally require a 1:2 wax to oil ratio, whereas the same degree of pliability can be obtained from the same single plant source beeswax freshly collected with a 1:1 ratio of wax and oil. By further example, any wax and oil combination will have a softer, more pliable composition when increased speeds of mixing are used. A 1:1 wax and oil blend which has been mixed at a high rate of speed may have equivalent smoothness to a 1:2 wax and oil blend which has been mixed at a slow rate of speed.

I have also now found, through further experimentation and discovery, that novel colloidal suspensions suitable for use as skin lotions and skin creams can be made using materials disclosed in my previous Application.

I have further found, through experimentation and discovery, that novel colloidal suspensions suitable for use as edible products can be made using materials disclosed in my previous Application.

I have further found, through experimentation and discovery, that novel compositions of the present invention have utility in promoting and accelerating the healing of injured tissue including burns, abrasions, cuts, lacerations, and the like.

BACKGROUND OF THE INVENTION

1) Field of Invention

The present invention is concerned with novel compositions containing fresh, unweathered, non-degraded beeswaxes from single plant sources (or from mixed plant sources) together with an oil and water, and the utilization of such compositions for the treatment of skin in animals including man.

The present invention is concerned with novel compositions containing fresh, unweathered, non-degraded beeswaxes from single plant sources (or from mixed plant sources) together with an oil and water, and the utilization of such compositions for the topical application to the skin of animals including man.

The present invention is concerned with novel compositions containing fresh, unweathered, non-degraded beeswaxes from single plant sources (or from mixed plant sources) together with oil and water, in the formation of colloidal suspensions, and the utilization of such compositions for the treatment of skin.

The present invention is concerned with novel compositions containing fresh, unweathered, non-degraded beeswaxes from single plant sources (or from mixed plant sources) together with oil and water, in the formation of colloidal suspensions, and the utilization of such compositions for topical application to the skin of animals including man.

The present invention is concerned with novel compositions containing fresh, unweathered, non-degraded beeswaxes from single plant sources (or from mixed plant sources) together with oil and water, in the formation of colloidal suspensions, and the utilization of such compositions as a lotion for topical application to the skin.

The present invention is concerned with novel compositions containing fresh, unweathered, non-degraded beeswaxes from single plant sources (or from mixed plant sources) together with oil and water, in the formation of colloidal suspensions, and the utilization of such compositions as a cream for topical application to the skin.

The present invention is concerned with novel compositions containing fresh, unweathered, non-degraded beeswaxes from single plant sources (or from mixed plant sources) together with oil and water, in the formation of colloidal suspensions, and the application of such compositions to the skin to facilitate improved softening of the skin.

The present invention is concerned with novel compositions containing fresh, unweathered, non-degraded beeswaxes from single plant sources (or from mixed plant sources) together with oil and water, in the formation of colloidal suspensions, and the application of such compositions to the skin to facilitate improved moisturizing of the skin.

The present invention is concerned with novel compositions containing fresh, unweathered, non-degraded beeswaxes from single plant sources (or from mixed plant sources) together with oil and water, in the formation of colloidal suspensions, and the application of such compositions to the skin to facilitate an improved rate of healing of the skin.

The present invention is concerned with novel compositions containing fresh, unweathered, non-degraded beeswaxes from single plant sources (or from mixed plant sources) together with oil and water, in the formation of colloidal suspensions, and the application of such compositions to the skin to facilitate a reduction in wrinkling of the skin.

The present invention is concerned with novel compositions containing fresh, unweathered, non-degraded beeswaxes from single plant sources (or from mixed plant sources) together with oil and water, in the formation of colloidal suspensions, and the application of such compositions to the skin to facilitate improved absorption of medications.

The present invention is also concerned with novel compositions containing fresh, unweathered, non-degraded beeswax from single plant sources (or from mixed plant sources) together with oil and water for use as a preventative aid for sunburn, windburns, skin chapping, chafing and the like.

Further, the novel compositions of the present invention have utility in promoting and accelerating the healing of burns, abrasions, minor cuts, scratches, dry skin, chapped skin, wind burned skin, friction-type burns, chafing and the like.

The present invention is also concerned with novel compositions for use as an analgesic to be applied topically for the treatment and alleviation of pain in the skin and underlying tissues, and mucous membranes.

The present invention is directed to novel compositions for use as a topical application to irritations of the skin and mucous membranes, including dry lips, chapped skin, minor abrasions, and the like, and irritated mucous membranes.

The present invention is also concerned with novel compositions for use as a base to which may be added other agents also promoting treatment, moisturization, or preventive measures for the skin.

The present invention is also concerned with a novel beeswax material for use as a base to which may be added other agents also promoting treatment, moisturization, or preventive measures for the skin, and many other uses and improvements made possible by the improved pliability, softness, and consistency of the single plant source beeswax-containing base.

The present invention is also concerned with novel compositions containing fresh, unweathered, non-degraded beeswaxes from single plant sources (or from mixed plant sources) together with oil and water, in the formation of colloidal suspensions, and the utilization of such compositions as edible food products, including use as a moisturizing, smoothing, and softening agent, and use as a butter or margarine substitute.

The present invention is concerned with novel compositions containing virgin beeswaxes from single plant sources (or from mixed plant sources) together with an oil, and the utilization of such compositions for the treatment of skin in animals including man.

The present invention is concerned with novel compositions containing virgin beeswaxes from single plant sources (or from mixed plant sources) together with an oil, and the utilization of such compositions as treatment for first, second, and third degree (partial and full thickness) burns due to sunburn, windburn, scalds, flash flame, electrical contact, chemical contact, cold, and the like.

The present invention is also concerned with novel compositions containing virgin beeswax from single plant sources (or from mixed plant sources) together with an oil for use as a preventative aid for sunburn, windburns, skin chapping, chafing and the like.

Futher, the novel compositions of the present invention have utility in promoting and accelerating the healing of burns, abrasions, cuts, lacerations, scratches, dry skin, chapped skin, wind burned skin, friction-type burns, chafing and the like.

The present invention is directed to novel compositions for use as a topical application to any irritation of the skin, including dry lips, chapped skin, abrasions, and the like.

The present invention is also concerned with novel compositions for use as an analgesic to be applied topically for the treatment and alleviation of pain in the skin and underlying tissues.

Further the present invention is concerned with novel compositions for use as a protective barrier between the skin and other irritants, eg, saliva, urine, fecal material, various chemical irritants and the like.

The present invention is also concerned with novel compositions for use as a base to which may be added other agents also promoting treatment, moisturization, or preventive measures for the skin.

2) Description of the Prior Art

Beeswax has been utilized in lotions and other compositions for many years. Its uses are described in both the patent literature and in other information sources as an ingredient in cosmetics, lotions, lip balms, lip sticks, creams, ointments, and other skin care products as well as in food stuffs, and in everything from shoe and furniture polishes to pharmaceutical preparations.

While acknowledging this information, Applicant has found that fresh, unweathered, non-degraded beeswax from a single plant source (or from mixed plant sources) has useful and surprisingly beneficial properties as is defined herein below.

I define over the prior Art by the term, fresh, unweathered, nondegraded beeswax. Such beeswax comprises a beeswax collected from comb which is generally 2–6 weeks since being drawn out by bees, is generally removed from the frame and collected after the first honey collection cycle, and is stored at low temperatures after removal of comb from the frame and obtaining the beeswax. Fresh beeswax may be obtained from comb drawn out by bees who have had access to one or more plant sources.

A more specialized beeswax is a fresh wax which is also a single plant source beeswax. This beeswax is obtained from comb which was drawn out by bees while they have had access to only one plant source.

As is used herein, the term "fresh beeswax" is defined as fresh, unweathered, non-degraded wax without distinction as to plant source or sources, and therefore includes single plant source beeswaxes.

Single plant source beeswax is the beeswax of the prior application (Ser. No. 825,657); it is also a fresh beeswax. Single plant source beeswaxes have all the properties of fresh beeswaxes. In addition, single plant source beeswaxes have unique properties of color and consistency that vary according to plant source.

The terms commercial, white, or yellow beeswaxes refer to beeswaxes of the prior Art.

The fresh beeswax of the instant invention is improved over waxes of the prior Art, in properties of improved pliability and softness, and improved ability to blend with the skin and mucous membranes.

The applicant has found the properties achieved when fresh beeswax is used in cosmetics, lotions, polishes, pharmaceutical preparations, food products and the like is unanticipated by the prior Art.

The compositions produce greatly increased softness and pliability of the fresh beeswax, ability to incorporate large amounts of oil into products without imparting a 'greasy feeling', ability to seemingly blend with and become part of the skin, thereby facilitating very rapid rates of healing of split, cut, torn, broken, or otherwise injured skin, and very rapid softening and smoothing of the skin.

Further, in compositions of edible food products, benefits include maintaining colloidal suspensions without imparting a sensation of 'waxiness' upon eating products containing the fresh beeswax. In addition, because single plant source beeswaxes can have many different colors, it is possible to prepare food products of the desired color without use or dyes or other coloring agents.

The wax of the instantly claimed invention is distinguished from the prior Art beeswaxes in that it is unmodified by contaminants, oxidation processes, cross-linking reactions, and the like, is softer and more pliable, and is generally not a wax from a reused comb.

Commercial beeswaxes, the beeswaxes of the prior art (called yellow beeswax, white wax, or pharmaceutical grade beeswax), are obtained as follows: As bees produce honey, they produce a waxy secretion which is drawn out into a comb in which honey, pollen, and progeny are stored. Since much of a bee's energy is consumed in the production of comb, the more comb production that occurs, the smaller will be the honey yield from a given amount of nectar source.

Therefore to maximize honey production, once bees have formed comb on a frame, the frames will be reused many times. This is accomplished in the following manner: When the comb in frames in a hive (or hives) are filled with honey, the frames are removed from the hive, the tops of each cell in the frames (the cappings) are cut off and the honey is removed from the comb by techniques such as gravity flow, centrifugal force, and the like. The frames containing empty comb are replaced in the hive, and the bees are moved to a new nectar source, where the bees fill the existing combs with honey, seal off the tops of each cell with new comb, and thusly very little new comb is produced and substantially all energy goes into honey production.

In the manner described above the cappings are again removed and the honey is collected. This cycle of filling empty cells, removing cappings, collecting honey and replacing empty frames is repeated many times. The process continues until such time as the comb is unuseable, generally 1–5 years. Each time honey is collected by a beekeeper, the oldest, unuseable comb is removed from frames after honey collection, combined with cappings, and used for production of beeswax.

This old comb is very different in characteristics and properties from the fresh, unweathered, non-degraded comb and single plant source comb that was originally drawn out by the bees. The once new comb has been subjected over time to extremes of temperature, moisture, sunlight, darkness, and has undergone physical, and oxidative, enzymatic, and other chemical changes. In addition, there has been repeated introduction of many different plant residues and resins, a buildup of bee metabolic products, and repeated applications of thin films of honey to the interior of the comb which has impregnated and altered the wax, and has hardened by the time more honey was added. Repeated use of smoke to allow access to the hives, settling of dust, dirt, debris, and pollen, and fluctuations in air quality also introduced contaminants to the comb. By the time the old comb is so foul it can no longer be used for honey production, it is dark to black in color, and very different in properties from new comb.

Generally beekeepers will rotate the age of empty comb frames in their hives so that many ages of comb are present among the hives at any given time. With every honey collection cycle, a few combs are removed and replaced with empty frames. Most beekeepers achieve a gradual replacement of all frames over a 5-year period.

The discarded comb is combined with cappings to form the raw material for beeswax production. The cappings themselves are blends of new and old wax. Bees draw up old wax into the cappings in addition to depositing new wax. In addition a part of the old comb is removed with the cappings when the beekeeper cuts, slices, or tears the cappings from the rest of the comb.

The comb and cappings are melted together, and large amounts of impurities are produced as scum and sludge. The impurities are reduced by skimming, straining, washing, decanting and the like. The purer portions of the wax are poured into molds and allowed to harden into blocks. Several melt/harden cycles may be involved. In the production of pharmaceutical grade wax and white wax, the wax is also bleached, or treated in other ways in order to remove all coloring agents.

Although impurities are removed by the above processes, 100% removal of impurities is not achieved, and the physical and chemical changes which have taken place during reuse of the comb are not reversed in the purification process, but are further accelerated, especially as a result of color removal procedures. Physical and chemical changes also continue to occur in the beeswax of commerce during the months between pouring into molds to form into blocks of beeswax and the final use, eg, incorporation into a product, during which time storage is at ambient temperatures in warehouses.

The final commercial beeswax product is known as yellow beeswax or if bleached, white wax. White wax is used as pharmaceutical grade wax. In the present application, the terms yellow, white, pharmaceutical, or commercial beeswax will refer to the above described beeswax products (known in the art); as described above these products are all prepared from old comb and cappings.

Contrary to the teachings of the prior art regarding the above described commercial beeswaxes, the applicant has found that fresh beeswaxes have useful and surprisingly beneficial properties as is defined herein below.

The wax of the instantly claimed invention is obtained by setting empty frames (with or without a layer of starter comb) in a hive, and then removing the frames as soon as the comb is drawn out by the bees. This generally requires 2–6 weeks. The honey is removed from the comb, and then the comb is removed from the frame. As much as is possible, incorporation of starter wax is avoided. Once the comb is removed, the comb is processed to wax, or it is placed in frozen storage until it can be processed. The comb is subjected to steps of washing, melting, filtration, and the like to produce the beeswax of the desired invention. Cappings alone, without incorporation of old comb, may also be used to produce a composition with the desired properties.

Once the beeswax has been separated from scum, debris, and the like, the wax is immediately used in the preparation of a final product, often while still hot and liquid from the first purification steps. If storage is required, the wax is cooled, and then placed in frozen storage until it is used.

It has been found that the wax of the above described process, henceforth called fresh beeswax has surprisingly different properties than the beeswax previously known in commerce.

It is within the purview of the invention to obtain waxes by other methods but having similar properties to the waxes obtained by the foregoing method.

A more specialized beeswax product is a beeswax obtained from a single plant source. Single plant source beeswax is obtained by setting empty frames in a hive, placing the hive in an area where the bees have access to one plant source, and then removing the frames most preferably as soon as the comb is drawn out by the bees. The honey is removed from the comb, and then the comb is subjected to steps of washing, melting, and the like to produce the beeswax of the desired invention. Single plant source beeswax is a fresh beeswax because it must be collected before a second blossom source is available, this generally precludes any reuse of the comb after the first honey cycle. However, single plant source beeswax differs from other fresh beeswaxes in that a single plant source beeswax is produced while bees have access to primarily one plant source. The result is that each single plant source wax is unique in color, consistency, malleability, and overall properties, and these properties are influenced by the plant source of the bees at the time the comb was produced by the bees.

In the above referenced application, a single plant source beeswax was described, and is effective in the present invention. These waxes have the properties described above; however, similar waxes obtained from areas where bees would have access to more than one plant would also have the desired properties, provided that they are fresh beeswaxes.

Beeswaxes, such as pharmaceutical grade beeswaxes, and oils have been included as ingredients in ointments and salves for treatment of burns for many years; however their use has been as a carrier for other chemicals which were the active ingredients for relief of pain and promotion of healing. Hence the designation of beeswaxes in the US Patent Office Classification System as "Designated Organic Nonactive Ingredient Containing Other Than Hydrocarbons". No use of prior art beeswaxes indicates potential for healing and skin treatment. As an ingredient in a composition base, beeswax has been used only as a vehicle for the application of other active ingredients. In the present invention the novel beeswax containing compositions are not only effective skin treatments, but by virtue of their effectiveness, also promote and increase the effectiveness of other active ingredients which the present invention can be used to deliver to an affected area.

The comb used to produce the prior art beeswaxes is different in characteristics and properties from new or "virgin" comb. The once new comb has been subjected over time to extremes of temperature, moisture, sunlight, darkness, and has undergone physical, and oxidative, enzymatic, and other chemical changes. In addition, there has been repeated introduction of many different plant residues and resins, a buildup of bee metabolic products, and repeated applications of thin films of honey to the interior of the comb which has impregnated and altered the wax, and has hardened by the time more honey was added. Repeated use of smoke to allow access to the hives, settling of dust, dirt, debris, and pollen, and fluctuations in air quality also introduced contaminants to the comb. By the time the old comb is so foul it can no longer be used for honey production, it is black in color, and very different in properties from new comb.

Contrary to the teachings of the prior art regarding the above described commercial beeswaxes, the applicant has found that a virgin beeswax has useful and surprisingly beneficial properties as is defined herein below.

The applicant has found that the beeswax of the previously described invention, together with an oil of choice, can be used without the aid of any other ingredients (although use of other ingredients is not precluded), as an ointment for the effective treatment of skin. This ointment is effective for treatment of burns, for the elimination of pain, for rapid removal of the sensation of heat from the site of a burn, for rapid reduction in tenderness, rapid promotion of healing of wounds, and prevention of fluid buildup and swelling at the site of an injury.

The wax of the instantly claimed invention is obtained by setting empty frames in a hive, and then removing the frames most preferably as soon as the comb is drawn out by the bees. This generally requires 2-3 weeks. The honey is removed from the comb, and then the comb is subjected to steps of washing, melting, and the like to produce the beeswax of the desired invention. Cappings alone, without incorporation of old comb, may also be used to produce a composition with the desired properties.

It has been found that the wax of the above described process, henceforth called virgin beeswax has surprisingly different properties than the beeswax previously known in commerce. It is an effective treatment for the skin, promotes rapid healing of wounds, and promotes rapid healing of burns and other skin abrasions.

In the above referenced application, a single plant source beeswax was described, and is effective in the present invention. These waxes have the properties described above; however, similar waxes obtained from areas where bees would have access to more than one plant would also have the desired properties, provided that they are virgin beeswaxes.

OBJECTS OF THE INVENTION

It is one object of the present invention to provide a composition for the treatment of skin in animals including man. Such composition is rendered truely hypoallergenic since no other ingredients other than fresh beeswaxes, and oil(s), with or without water are required to achieve the desired benefits.

Another object of the present invention is to find a novel composition having utility as a salve, balm, ointment, cream, lotion, emollient and the like, for topical application to the skin of animals including man.

It is a further object of the present invention to provide a composition for improved softening of the skin.

It is a further object of the present invention to provide a composition for improved moisturizing of the skin.

It is a still further object of the present invention to provide a composition for an improved rate of healing of the skin.

It is an additional object of the present invention to provide a composition for a reduction in wrinkling of the skin.

Further, an object of the present invention is to provide a composition for improved absorption of medications.

An additional objective of the present invention is to prevent sunburns, windburns, skin chapping, chafing, and the like by application of the novel composition according to the present invention.

It is also another object of the present invention to provide a composition for promoting and accelerating the healing of burns, abrasions, minor cuts, scratches, dry skin, chapped skin, sunburns, windburns, friction burns, chafing and the like.

In additional, it is an objective of the present invention to provide a composition for use as an analgesic to be applied topically for the treatment and alleviation of pain in the skin and underlying tissues, and in mucous membranes.

It is a further object of the present invention to provide a composition for use as a topical application to any irritation of the skin and mucous membranes, including dry lips, chapped skin, abrasions, and the like, and irritated mucous membranes.

Also it is an object of the present invention to provide an improved base for compositions existing in the prior art including those for the treatment of burns, chapped skin, dry skin, and the like, for moisturizing skin, for use in cosmetics, for administration of medications through the skin, and other compositions for topical application to the skin. The use of such improved compositions will improve the effectiveness of other ingredients and thus lessen the severity of other symptoms.

It is a further object of the present invention to provide a novel beeswax for use as a base to which may be added other agents.

It is an additional object of the present invention to provide a composition for use as edible food products, including use as a moisturizing, smoothing, and softening agent, and use as a butter or margarine substitute.

Further, it is an objective of the present invention to provide a novel beeswax for use in edible food products, including use as a moisturizing, smoothing, and softening agent, and use as a butter or margarine substitute.

It is one object of the present invention to find a novel composition having utility as a salve or ointment for the treatment of burns in animals including man by topical application of an ointment.

It is a further object of the present invention to provide a composition for the treatment of sunburns, windburns, and the like.

An additional objective of the present invention is to prevent sunburns, windburns, and the like by application of the novel composition according to the present invention.

It is a further object of the present invention to provide a composition for the alleviation of pain due to burns and abrasions, ie, analgesic.

It is an object of the present invention to provide an ointment for the treatment of chapped skin.

It is a further object of the present invention to provide a composition for use in the treatment of skin abrasions.

It is an additional object of the present invention to provide a novel composition for use as an improved protective skin barrier against bodily fluids, and other agents of irritation.

These and other objects will become apparent as objects of the present invention.

DESCRIPTION OF THE INVENTION

It has now been found that fresh beeswaxes can be combined with oil and water to prepare improved ointments and salves for the treatment of the skin. Specifically, uses include moisturizing, lubricating, softening, reduction of wrinkling of the skin, promotion of healing of burns and abrasions, a composition to facilitate the administration of medications and other pharmaceutical agents, and an improved base for compositions for topical application. It has also been found that fresh beeswaxes can be combined with water and oil to form edible food products, including margarines and butter substitutes, and to form ingredients in edible food products.

According to the invention, it has been found that novel, heretofore undiscovered, beneficial properties can be obtained from combinations of novel beeswaxes with oil(s) and water. These novel beeswaxes are physically and chemically different from the beeswaxes of the prior art.

When combined with an oil, or a mixture of oils, and water, and mixed thoroughly, the beeswax of the present invention forms a soft, pliable composition suitable for use as an ointment, salve, cream, lotion, emollient, and other such material for topical application. The improvement being that the instant composition is more pliable than compositions of the prior art, and upon skin contact is much more effective as a skin moistener, skin softener, burn treatment, burn preventive, and general skin treatment and protective agent. Its composition is especially soft because of its nature and its use is therefore facilitated. Although comprised of large quantities of oil, the present invention does not impart a greasy feel to the skin upon use in topical applications.

It is prefered that all (100%) of the beeswax used in the present invention be fresh beeswax. The term fresh beeswax, refers to beeswax that is obtained from comb that is collected soon after it has been excreted and drawn out by bees, preferably at or before the time of the first collection of honey. For example, fresh beeswaxes are obtained from comb that is eight weeks in age or less and that is collected at the time of the first collection of honey. As a further example, fresh beeswax can be obtained from cappings, provided that old comb is not combined with the cappings.

The moment beeswax is excreted by bees, processes of physical and chemical changes begin. The conversion of new comb to old comb, and the change from fresh beeswax to the "old" beeswaxes known in the prior art is gradual. Thus the shorter the time for these changes to occur, the more beneficial will be the properties of the resultant beeswax for purposes of the present invention. Conversely, the greater the opportunity for physical and chemical modification, the less beneficial are the properties of the beeswax for purposes of the present invention.

Thus while fresh beeswaxes produce preferred compositions, waxes produced from comb which have experienced a greater degree of physical and chemical modification may still have adequate (though not optimal) properties.

Equivalent results may be obtained with these other beeswaxes so long as the novel, beneficial properties of the combinations of beeswaxes, oil(s), and water are not substantially altered. For example, while less preferred, acceptable results may be achieved by the use of beeswaxes obtained from comb that has been in use for 9 months, with as many as six extractions of honey, provided these waxes are used immediately or are immediately stored at temperatures below 0° C. Other beeswaxes with substantially equivalent properties to those described for fresh beeswaxes, may also be used to provide the desired composition.

Any use of fresh beeswaxes in any composition, whether sole ingredient or minor ingredient will contribute novel, improved properties to the desired composition.

In the present invention, the fresh beeswax is combined with oil and water in proportions ranging from about 1:1/10:0 to about 1:20:20 by volume, with a preferred range of about 1:1:0 to about 1:6:6, by volume to produce a soft, easily applicable composition for topical application to the skin.

Formation of colloidal mixtures is readily accomplished by mixing ingredients in the liquid state and then cooling to desired temperatures, generally ambient or below, although any method of achieving the desired mixture, or solution, or suspension may be utilized. Cooling may be accomplished by ambient cooling or by use of an ice water bath or other means of temperature reduction known in the Art.

Use of a suitable surfactant is desireable in some circumstances, since such uses improve the stability of the colloidal suspension, assist in the incorporation of the water and oil or other ingredients into the suspension, and help to prevent loss of colloidal suspension due to coalescing of water.

To use the lotions and creams of the instant invention, small amounts are applied to the affected areas or any desired areas by applying the ointment onto the skin. Other methods of application, including but not limited to soft cloths, chamois, spray application and the like may also be used as methods of application.

For the preparation of edible food products, fresh beeswax is combined with oil and water in proportions ranging from about 1:1/10:0 to about 1:20:20 by volume, with a preferred range of about 1:1:0 to about 1:6:6, by volume, to form a soft product. When no surfactant or ather such agents are used, the most preferred proportions are 1:4:4, by volume of wax, oil, and water, for margarine-like products. The mixture is then placed in a tub.

Formation of colloidal mixtures is readily accomplished by mixing ingredients in the liquid state and then cooling to desired temperatures, generally ambient or below, although any method of achieving the desired mixture, or solution, or suspension may be utilized. Cooling may be accomplished by ambient cooling or by use of an ice water bath or other means of temperature reduction known in the Art.

Use of a suitable surfactant is desireable in some circumstances, since such uses improve the stability of the colloidal suspension, assist in the incorporation of the water and oil or other ingredients into the suspension, and help to prevent loss of colloidal suspension due to coalsecing of water.

The edible food product may be used with or without salt, although small amounts of salt are preferred.

While any fresh beeswax may be used in the preparation of a margarine, avocado wax or another fresh or virgin beeswax of yellow color is preferred so no additional coloring agent is needed in the final product.

Although single plant source beeswaxes can be obtained in various manners, the present inventor has utilized the method described in Example 1, as follows:

EXAMPLE 1

Empty frames or starter frames are placed in a beehive which is then placed in the center of an area with a very large nectar source of one plant source. The bees in the hive gather pollen and nectar from blossoms in the surrounding area and use it to produce comb, honey, and the like. When the comb has been drawn out, the frame(s) are removed from the hive. The honey is removed and the new comb is removed from the frame. From the time the empty frames are placed in the field to the time the combs are drawn out and ready for removal generally requires 2–6 weeks. The comb is immediately stored at temperatures below 0° C. until it is processed further.

The comb is then rinsed repeatedly with water by the steps of mixing a slurry of water and comb in a blender, decanting the water, and repeating the process until the honey is removed. The comb, now in small pieces, is placed on teflon sheets and dried in a dehydrator at a temperature sufficient to dry the comb without melting the wax. Suitable temperatures ranged from 85–145° F.

The dry comb is melted and while in the liquid state the impurities are removed from the wax by steps of decanting and skimming. The wax is then allowed to cool and solidify, and the wax is then stored at 0° C. or below.

The wax is then remelted. The liquid wax is combined with a suitable amount of the oil of choice and distilled water which have been separately heated to about the same temperature as the beeswax. The heated mixture is then allowed to cool and solidify while being continuously stirred mixed at mixing speeds necessary to produce a colloidal suspension. The suspension may require additional mixing after cooling to ambient temperatures to reincorporate any water which may coalesce. The mixture is then packaged for use and stored at temperatures below 0° C. Skin care preparations are packaged appropriately and stored at ambient temperatures during use. Edible food products are refrigerated or frozen during use.

Suitable plant sources of fresh beeswaxes are eucalyptus, sunflower, tupelo, cotton, safflower, avocado, thistle, alfalfa, clover, palmetto, orange blossom, gall berry, red maple, holly, apple blossom, cherry, blackberry, blueberry, olive, lahiua, sesame, rape, mustard, honey dew, buckwheat, blackgum, cactus, saguaro, prickly pear, anise, tulip poplar, sage, mint, pusley, lavendar, rosemary, thyme, salt cedar, tamarisk, paloverde, mesquite, Braziliam pepper, and the like. Combinations of plant sources may also be successfully used. Suitable oils or fats include almond, apricot kernel, avocado, coconut, corn, cottonseed, grapeseed, hazelnut, linseed, olive, palm, peanut, pumpkin seed, safflower, sesame, soy, sunflower, walnut, cocoa butter, bambuk butter, petrolatum, tonka bean butter, mineral oil, and the like. It is preferable to use an oil similar to the plant source of the wax. However, it is also within the perview of the invention to use many different types of oils or fats. Oils, fats, mixtures of oils and oils or fats (whether natural or synthetic, of animal or plant origin) bearing similar properties would be suitable for use in the present invention. Any suitable water source can be used, including distilled water, deionized water, spring water, tap water, filtered water, and the like.

The composition of the instantly claimed invention has the additional advantage of being hypoallergenic to a larger proportion of the population than other preparations. Containing no ingredients other than wax, oil, and water, there are fewer ingredients to cause allergic reactions. Further, sensitive individuals may avoid allergic reactions by selecting oils and waxes from well-tolerated sources.

For use in general as a topical composition for treatment or enhancement of the skin, the present invention is applied topically in amounts sufficient to cover the affected skin area completely, and is then massaged in gently. The application can be repeated as frequently as necessary or as desired.

For use as a sunburn preventive, the novel composition is generously applied, and massaged into all areas of the skin where sun exposure is expected to occur. The ointment is not removed in water and one thorough application will last for about one day, although it may be applied as frequently as desired. Similarly, the ointment may be used for prevention of windburns and the like.

For use as a treatment for sunburns, windburns and the like, the ointment should be applied within about 4 hours after the burn occurs. Liberal quantities of the ointment are applied to the affected areas and are gently massaged into the skin until all sensations of dryness, itching, and burning are eliminated. The ointment should be reapplied in the manner described about 4 times during the next 24 hours, and should be used as frequently as needed on any areas experiencing discomfort.

For use in the treatment of chapped lips or skin, after the affected area is washed and dried thoroughly, while taking care not to re-introduce any irritants, the ointment is applied topically to the affected area and gently massaged into the skin. The process is continued until all feelings of dryness, chaffing, and pain are eliminated. When chapping is severe, the ointment is reapplied as frequently as every 1–2 hours until the area is healed. For moderate or slight chapping, the ointment is applied once or twice each day until the area is healed. To prevent recurrance of chapping, the ointment may be reapplied every 1–3 days.

For use as an improved base for compositions in the prior art, the desired additional ingredients should be added to the present invention, and applied in a manner appropriate to the desired treatment. Conventional additives may be added to the novel composition, eg, surfactants, emulsifiers, coloring agents, vitamins, lanolin, aloe vera, perfumes, antibiotics, anaesthetics, and the like without detrimental effects on the desired properties of the present invention.

In the related application referenced above I disclosed compositions containing single plant source beeswaxes and oils for use as lip balms, lip sticks, and cosmetic preparations. The present invention concerns the use of beeswaxes, oils and water as a lotion or cream, and as a skin treatment and injury preventive aid, as well as in cosmetic preparations. The present invention also concerns the use of beeswaxes, oils, and water in edible food products.

EXAMPLE 2

SKIN CREAM FROM BEESWAX OF THE INSTANT INVENTION

Avocado beeswax, safflower oil, and distilled water were combined in the following proportions, by volume:

| | |
|---|---|
| avocado beeswax | 1 part |
| safflower oil | 2 parts |
| distilled water | 2 parts |

All ingredients were heated to 200° F., combined, and mixed while cooling to ambient temperatures. A colloidal suspension was formed as the wax began to solidify, and the colloidal suspension was maintained by mixing during cooling. The suspension was allowed to set for several hours and then was remixed at high speeds. The colloidal suspension thus formed was about the consistency of a hand cream and was light yellow in color.

EXAMPLE 3

The instant cream of Example 2 was applied to the hands of a female volunteer. Because of her occupation as a hairdresser, which included repeated shampooing and rinses, giving permanents and hair color treatments, the hands of the volunteer were rough, dry, cracked, and the skin was peeling.

The volunteer applied the instant cream of Example 2 on an intermittent, as desired, basis, for a period of 4 days. At the end of the 4-day period of application, the hands of the subject were examined. The skin on her hands was no longer peeling, the peeled areas were healed, and the skin was not rough and cracked.

EXAMPLE 4

SKIN LOTION FROM BEESWAX OF THE INSTANT INVENTION

Avocado beeswax, safflower oil, and distilled water were combined in the following proportions, by volume:

| | |
|---|---|
| avocado beeswax | 1 part |
| safflower oil | 4 parts |
| distilled water | 4 parts |

The above ingredients were combined and the lotion prepared according the the process described in Example 2, above.

The instant product thus formed was slightly thinner in consistency than that formed in Example 2. The lotion was shiny and light yellow in color.

EXAMPLE 5

LOTION FROM COMMERCIAL YELLOW BEESWAX

Commercial yellow beeswax, safflower oil, and distilled water were combined in the following proportions, by volume:

| | |
|---|---|
| commercial yellow beeswax | 1 part |
| safflower oil | 4 parts |
| distilled water | 4 parts |

The process described in Example 4 was repeated with idential proportions, ingredients, and procedures. As the only change, USP grade commercial yellow beeswax was substituted for single plant source avocado wax of the instant invention. The colloidal suspension formed with commercial yellow beeswax was creamy white in color, dryer in appearance and much thicker in consistency.

EXAMPLE 6

COMPARISON OF SAMPLES PREPARED WITH SINGLE PLANT SOURCE BEESWAX AND LOTIONS PREPARED WITH COMMERCIAL BEESWAX

A small amount of the lotion prepared with avocado beeswax as described in Example 4, was applied to the back of the left hand of a female subject in her early forties. She reported that the lotion felt very smooth and soothing, noted a slight, temporary, shiny appearance on the back of the left hand, and noted that there was a cool sensation as the lotion was massaged into the skin on the back of the hand. Within minutes she noted that the skin on the back of the left hand felt much less tight and much more supple.

At the same time an equal amount of lotion prepared from commercial USP yellow beeswax by the method of Example 5, was applied to the back of the right hand of the subject. The lotion was applied easily and smoothly, and there was a more dry appearance to the back of the hand. The temporary shiny appearance did not occur as the lotion prepared the commercial yellow beeswax was massaged into the skin. However, the subject reported that the skin of the right hand was also smoother and more supple.

After about 30 minutes, the subject noted a slight pulling and tingling sensation in the right hand (commercial beeswax formula). The skin on this hand was noticably drier and had a slight leathery appearance.

After the 30 minute period, the subject was instructed to avoid the use of any type of hand cream, lotion, ointment, or the like, and was then allowed to return to normal daily activities without further restrictions on use of either hand and without restrictions on type of activity.

After 6 hours, the subject noted that the right hand remained noticeably drier than the left hand. The left hand felt smooth and soft and pliable, while the skin on the right hand felt dry and stiff.

When the two hands were visually compared, the skin that had been treated with the instant invention was smoother and less wrinkled than the skin that had been treated by the commercial preparation.

Observations continued for a 72-hour period, during which time the subject continued a full range of normal activities, including occassional washing of both hands in soap and water, with the exception that no use of hand creams, lotions, ointments, and the like of any kind was allowed. The earlier noted differences in softness, suppleness, magnitude of wrinkles and skin folds, itching and irritation continued during that period of time.

After the 72-hour period, the subject noted that the sensation of dryness and irritation in the right hand was greater than it had been on the first day of the test. The skin of the right hand (to which lotion prepared from commercial yellow beeswax was applied) was drier, more leathery, was noticeably more wrinkled, and felt itchy, irritated, and uncomfortable. The skin of the left hand (to which the lotion of the instant invention was applied) was smooth, soft, and felt comfortable three days after the one-time application.

EXAMPLE 7

MARGARINE-LIKE PRODUCT FROM BEESWAX OF THE INSTANT INVENTION

A margarine-like product was prepared by combining avocado beeswax, safflower oil, and distilled water in the following proportions, by volume:

| | |
|---|---|
| avocado beeswax | 1/4 cup |
| safflower oil | 1 cup |
| distilled water | 1 cup |
| salt | 1/2 tsp |

The beeswax, oil, and water were heated until they were above the melting point of the beeswax. The wax, oil, and water were than mixed intermittently while being allowed to cool to ambient temperature. As the temperature decreased, a colloidal suspension began to form. The colloidal suspension was maintained by intermittent mixing during cooling. The suspension was allowed to set for several hours and then was remixed at high speeds and salt was added to taste. The product thus formed was a colloidal suspension that was very soft in consistency, shiny, and light yellow in color and appearance. The margarine-like product was suitable for use as a spreadable product in a tub. With the formula provided in this example, the taste was smooth and margarine-like and there was no wax-like taste imparted by the product.

Other margarine-like products were prepared which had greater proportions of wax present. These formed firmer, less soft, products; however, beeswax could be tasted in these margarine-like products, and small amounts could be felt on surfaces of the teeth. Therefore, the above formulation was preferable.

EXAMPLE 8

MARGARINE-LIKE PRODUCTS FROM COMMERCIAL YELLOW BEESWAX

The procedures described in Example 7 were repeated with idential proportions, ingredients, and procedures. As the only change, USP grade commercial yellow beeswax was substituted for the single plant source avocado wax of the instant invention. The colloidal suspension formed was creamy white in color, and was much more dense in consistency.

When the margarine-like product of Example 8 was tasted, a thin film (most probably a thin film of commercial yellow beeswax) coated the upper surface of the mouth. Such a film was not observed with the margarine-like product of the instant invention.

It has further been found that fresh, new or 'virgin' beeswaxes can be combined with an oil alone to prepare still more ointments and salves and the like for the treatment of the skin. Specifically, uses include treatment of burns and abrasions, prevention of burns, a protective barrier for the skin, a composition to facilitate the administration of medications and other pharmaceutical agents, and an improved base for compositions for topical application.

According to the invention, it has been found that novel, heretofore undiscovered, beneficial properties can be obtained from novel combinations of beeswaxes and oils. Unlike beeswaxes of the prior art, the virgin beeswaxes of the present invention have had minimal contact with plant residues and resins, minimal exposure to environmental forces of temperature fluctuations, humidity, dust and debris, air pollutants, minimal opportunities for oxidative processes and other physical and chemical changes. These novel beeswaxes are, therefore, physically and chemically different from the beeswaxes of the prior art.

When combined with an oil or a mixture of oils, the beeswax of the present invention forms a soft, pliable composition suitable for use as an ointment, salve, cream, and other such material for topical application. The composition is more pliable than compositions of the prior art, and upon skin contact is much more effective as a skin moistener, skin softener, burn treatment, burn preventive, and general skin treatment and protective agent. Its composition is especially soft because of its nature and its use is therefore facilitated. The composition requires less oil to achieve the desired pliable state than compositions of the prior art waxes. Thus, although comprised of large quantities of oil, the present invention does not impart a greasy feel to the skin upon use in topical applications.

While virgin beeswaxes produce preferred compositions, waxes produced from comb which have experienced a greater degree of physical and chemical modification may still have adequate (though not optimal) properties.

Any use of virgin beeswaxes in any composition, whether sole ingredient or minor ingredient will contribute novel, improved properties to the desired composition.

In the present invention, the beeswax described above is combined with an oil in proportions ranging from 1:1/10 to 1:10 by volume, preferably 1:1 by volume to produce a relatively soft, easily applicable composition for topical application to the skin. Small amounts are transferred to the hands and applied to the affected areas or any desired areas by gently massaging the ointment onto the skin. Other methods of application, including but not limited to soft cloths, chamois, spray application and the like may also be used as methods of application.

Although it is preferred that 100% of the beeswax used in the present invention be virgin beeswax, acceptable results may be achieved by the use of combinations of virgin waxes, cappings, and other waxes, such as the commercial beeswaxes of the prior art. Virgin beeswaxes and cappings may be used in any desired proportions, from 100% virgin beeswax to 100% cappings. In the proportions below for virgin beeswax, cappings may be used to replace any part or all of the virgin beeswax. The ratio of virgin beeswax to commercial beeswaxes ranges from 1:2 to 1:0 parts by volume with the ratio of at least 1:1 by volume preferred, and the ratio of 1:0 by volume most preferred.

Although the composition according to the present invention can be obtained in various manners, the present inventor has utilized the method described previously in Example I, with the addition that after the melted wax is purified as described, the melted wax and oil are combined directly to form the product, without the steps of allowing the wax to cool and solidify and then subsequent remelting.

For use in general as a topical composition for treatment or enhancement of the skin, the present invention is applied topically in amounts sufficient to cover the affected skin area completely, and is then massaged in gently. The application can be repeated as frequently as necessary or as desired.

For use as a sunburn preventive, the novel composition is generously applied, and massaged into all areas of the skin where sun exposure is expected to occur. The ointment is not removed in water and one thorough application will last for about one day, although it may be applied as frequently as desired. Similarly, the ointment may be used for prevention of windburns and the like.

For use as a treatment for sunburns, windburns and the like, the ointment should be applied within about 4 hours after the burn occurs, although the ointment may be applied after the four-hour period. Liberal quantities of the ointment are applied to the affected areas and are gently massaged into the skin until all senataions of dryness, itching, and burning are eliminated. The ointment should be reapplied in the manner described about 4 times during the next 24 hours, and should be used as frequently as needed on any areas experiencing discomfort.

For use in the treatment of more serious burns such as those due to contact with very hot items, flames, or high temperatures, the ointment is applied in a thick layer as a salve. Thickness may be any desired depth; a thickness of 1/32 inch to 1/8 inch is preferred. The ointment should be smoothed over the affected area by hand or with any smooth-surfaced applicator. Gentle spreading should continue until pain disappears. Alternatively, many applications of ointment are gently massaged onto the burned area until the sensations of heat and pain are relieved; this generally requires about 20 minutes.

For several hours after the application of the ointment, the pain will return instantly if the area is even lightly touched or scratched. This is relieved by applying more ointment and massaging the area again for a few minutes. Generally after a period of about four hours, the area will no longer be sensitive to touch.

For friction burns, the affected area is treated as described above for skin burns.

For use in the treatment of chapped lips or skin, after the affected area is washed and dried thoroughly, while taking care not to re-introduce any irritants, the ointment is applied topically to the affected area and gently massaged into the skin. The process is continued until all feelings of dryness, chaffing, and pain are eliminated. When chapping is severe, the ointment is reapplied as frequently as every 1–2 hours until the area is healed. For moderate or slight chapping, the ointment is applied once or twice each day until the area is healed. To prevent recurrance of chapping, the ointment may be reapplied every 1–3 days.

For use as an analgesic, the present invention is applied topically in amounts sufficient to cover the affected skin area completely, and is then massaged in gently. The application is repeated continually until the pain, discomfort, and all sense of dryness are eliminated. On average 2–20 minutes are required to achieve complete relief. If pain should return (as in the case of accidental brushing against a recently burned area), the above process is repeated until the pain again is eliminated.

For use in the treatment of skin abrasions, the affected area is carefully cleaned of any dirt and debris, and washed and rinsed thoroughly. If desired a small amount of antibiotic is also applied. The present invention is then applied topically in amounts sufficient to cover the affected skin area completely, and is then massaged in gently. The process is continued until the heat from the affected area and the pain is eliminated. The application is then repeated as frequently as desired.

For use an a protective skin barrier against bodily fluids and other agents of irritation, the area to be protected is first washed thoroughly to remove any traces of irritating materials. The area is thoroughly dried, while taking care to avoid any contact with irritating substances. The present invention is then applied topically in generous amounts sufficient to cover the affected skin area completely, and is then massaged in gently. To maintain a protective barrier, the process of washing, drying and reapplication should be repeated 2–4 times each day.

For use as an improved base for compositions in the prior art, the desired additional ingredients should be added to the present invention, and applied in a manner appropriate to the desired treatment. Conventional additives may be added to the novel composition, eg, surfactants, emulsifiers, coloring agents, vitamins, lanolin, aloe vera, perfumes, antibiotics, anaesthetics, and the like without detrimental effects on the desired properties of the present invention.

In the related application referenced above I disclosed compositions containing single plant source beeswaxes and oils for use as lip balms, lip sticks, and cosmetic preparations. The present invention concerns the use of beeswaxes and oils as a skin treatment and injury preventive aid, as well as in cosmetic preparations.

In addition to the invention described in my previous application, which includes single plant source beeswaxes, the present invention describes compositions which include virgin beeswaxes obtained from multiple plant sources in the cosmetic, skin treatment and injury preventive applications.

EXAMPLE 9

A fair-skinned, four year old child experienced sunburn on his ears from exposure to bright sunlight for an eight-hour period. The most exposed portions of the ears had turned purple in color and were hot, dry, and painful to the touch. About 90 minutes after the exposure period ended, a salve containing equal parts (1:1) by volume of virgin beeswax and oil was applied to the sunburned areas by the following process: the right index finger was rubbed across the top of the ointment, and a small amount of the ointment was thusly transferred to the index finger. The ointment was then applied to the affected area by gently rubbing and massaging the area. Repeated applications were made for a ten minute period until the affected areas no longer felt hot, dry, or painful.

After the ten minute period of application, no further use of the ointment was required. Over the next twelve hours the purple color faded to normal skin tone. The child experienced no blistering or peeling of the previously sunburned skin, no burning or discomfort, no dryness, itching, or other symptoms associated with sunburn.

EXAMPLE 10

A very fair skinned, red-haired child (who had not been conditioned to sun exposure) experienced sunburn after playing for four hours in bright, midday sunlight at an ocean beach. The skin was completely unprotected, and no sun screen ointments or salves of any type were used. At the end of this time period, the child's face was bright, angry red in color; the condition of the hot, dry, irritated skin, indicated that the child had experienced a severe sunburn.

The ointment of the instantly claimed invention was applied to the child's face immediately after the four-hour exposure period. The method of application was as described in Example 9. However, the ointment was applied to the face about four times during the 24-hour period immediately following the sun exposure.

One spot on the child's face, an area about the size of a dime just below the lower lip, did not seem to be red, and appeared to not be sunburned. This area was not treated in any way.

In the areas of the face where the ointment of the instantly claimed invention was applied, no blistering, peeling or the like occurred. The skin simply faded to normal skin tone during the 24-hour period following the intense sun exposure. After the first application of the instantly claimed invention, the skin no longer felt hot to the touch and no longer felt dry. The child had no complaints of discomfort and carried out all normal childhood activities.

The small, untreated area of skin blistered so severely that the skin developed scabs, and required about one week to heal completely.

EXAMPLE 11

Ten fair skinned people applied the ointment of the instantly claimed invention to their skin just prior to several hours of exposure to direct sunlight. The method of application was as described in Example 1. No other method of skin protection was used. During the sun exposure, activities of the subjects included sunbathing and swimming.

After the exposure period, no individual experienced sunburn symptoms. The skin remained soft, pliable, and normal in skin tone, except that a slight tanning of the skin was noted. No pain, tingling, itching, dryness, burning, or other irritation was reported. One individual who normally experienced small hives in sun exposed areas, reported no effects of exposure.

One fair skinned individual, continued to use the ointment and was able to achieve a nice tan for the first time in her life.

EXAMPLE 12

A forty-seven year old woman received a burn approximately 3 cm in diameter on her arm while removing a pan from her oven. The burned area blistered immediately, and then the blister popped immediately. The pain the individual experienced was intense.

The affected area was immersed immediately in cold water for about five minutes. Following this, the ointment of the instantly claimed invention was applied to the affected area in the manner described in Example 9. The ointment was applied to the area and gently massaged into the skin repeatedly during the next 20 mintues. By the end of this time period, the pain from the burn was completely gone, and although the wound definitely remained, the sensation was as if the burn had not occurred.

Over the next three days the area of the burn healed rapidly and completely.

EXAMPLE 13

A thirty-nine year old woman experienced an oven burn about 2 cm in diameter. The area was reddened, painful, and slightly blistered. The ointment of the instantly claimed invention was immediately applied to the affected area in the manner of Example 9. The ointment was applied repeatedly for about 15 minutes, with gentle massaging and rubbing to distribute the ointment thoroughly and to mix it well with the tissues in the burned area.

After the fifteen minute period, the woman reported a complete cessation of pain, and that the affected area felt as if it had never been injured. During the next four hours, even a slight touching of the affected area would bring back a sudden return of the pain and intense burning sensation. Each time this occurred, the ointment was reapplied to the area and massaged for about one minute, and the pain and all sensation of injury would again disappear.

After about four hours, the area was no longer sensitive to touch, and all normal use of the affected area was resumed. No further blistering, other than the small initial blisters occurred.

During the next week the skin at the affected area gradually turned darker and took on a waxy and somewhat leathery appearance. About two weeks after the initial burn occurred, this waxy, leathery skin peeled off, and the area underneath was new skin, completely healed.

During the two-week process, there was no discomfort, no loss in any function or ability to use the affected area, and no need for any bandage.

EXAMPLE 14

A 22 year old woman experienced a painful burn from boiling jam. An area on her hand approximately 4 cm in diameter was reddened and intensely painful. About 2 minutes after the accident, the ointment of the instantly claimed invention was applied to the area of the burn. The method of application was as described in Example 9. The ointment was applied and massaged into the burned area continuously for about 20 minutes. During this period the individual reported that the sensations of heat and intense pain were lessening. After about 20 minutes, the individual reported that she had no sensations of any discomfort and resumed her normal activities.

EXAMPLE 15

A women with chapped hands, and deep cracks at the knuckles and around the base of the fingers had been unable to find any preparation (ointment, salve, medication) which could successfully promote healing of her dry, painful hands. She was given the ointment of the present invention, and applied it to her hands by the method described in Example 9. Within four days her hands were completely healed. She continued daily use of the ointment of the present invention and reported that no further problems with dryness and cracking occurred.

EXAMPLE 16

A 38-year old woman received an abrasion on the knee which resulted from a fall. Small amounts of fine, oily, dirty particles were imbedded in the area, and she experienced a friction burn in the same area. The knee was swollen, the skin was oozing, very tender, very painful, hot to the touch, and the knee could not be moved without pain from stretching the skin. The ointment was applied on the second day after the injury because the pain and tenderness, and the heat in the area had not subsided. Within 30 minutes after application, the heat in the area was eliminated, and the knee could be moved without pain to the skin. The ointment was reapplied about 4 times daily for two days. The injury healed rapidly after application of the ointment was begun, and the wound was healed in two days.

EXAMPLE 17

A 41-year old male received a third-degree burn to three fingers on each hand. The burn occurred when he attempted to pick up and pull a hot stove burner coil out from the top of a range. The subject described intense pain after the burn. On examination, there was an area approximately 1.2 cm in diameter on each finger where the skin was white, dry, and appeared charred. No blistering was observed.

Within two minutes, the ointment was applied to the burns in thick layers. Gentle massaging was used to apply the ointment, and then a smooth spatula was used to spread the ointment evenly and completely over the area to a depth of about ⅛th inch. Within 20 minutes, the subject reported that all pain was gone, and he was careful to avoid any contact with the injured tissues for the next four hours. After this time the subject resumed his normal activities. No other treatments or bandaging were employed; no additional application of ointment was used. Over a period of two weeks, the charred skin gradually sloughed off, and the skin beneath was completely healed. There was no swelling, redness, irritation, or tenderness observed at any time during the healing process. There was also no oozing, scab formation or scarring.

In its use as a composition for the treatment of skin in animals including man, it is clear that many other ingredients may be added to the present invention without detracting from the intent of the present invention. Such additional ingredients would include any desired active ingredients, herbal or other natural products or their equivalent, vitamins, anaesthetics, antibiotics, analgesics, extenders, preservatives, binders, fillers, dyes, pigments, perfumes, colorants, emulsifiers, surfactants, and the like. Such ingredients may be added to the present invention which would serve as a composition base and by the nature of its properties further enhance the effectiveness of the other ingredients. In addition some may be combined with the present invention to modify its mode of application, its viscosity, and the like.

It is clear that many other ingredients may be added to the present invention without detracting from the intent of the present invention as a composition for the treatment of burns. Such additional ingredients would include any desired active ingredients, healing promoters, anaesthetics, antibiotics, analgesics, vitamins, zinc oxide, and the like to provide for a further enhanced burn treatment, in addition to the use of fillers, extenders, preservatives, binders, dyes, perfumes, colorants, emulsifiers, surfactants, and the like. Such ingredients may be added to the present invention which would serve as a composition base and by the nature of its properties further enhance the effectiveness of the other ingredients.

It is clear that many other ingredients may be added to the present invention without detracting from the intent of the present invention as a composition for the treatment of sunburns, windburns, and the like. Such additional ingredients would include lanolin, aloe vera products, vitamins, zinc oxide, anaesthetics, antibiotics, analgesics, and any other desired active ingredients, fillers, extenders, preservatives, binders, dyes, perfumes, colorants, emulsifiers, surfactants, and the like. Such ingredients may be added to the present invention which would serve as a composition base and by the nature of its properties further enhance the effectiveness of the other ingredients and compositions.

It is clear that many other ingredients may be added to the present invention without detracting from the intent of the present invention as a composition for the treatment of burns. Such additional ingredients would include any desired active ingredients, healing promoters, anaesthetics, antibiotics, analgesics, vitamins, zinc oxide, and the like to provide for a further enhanced burn treatment, in addition to the use of fillers, extenders, preservatives, binders, dyes, perfumes, colorants, emulsifiers, surfactants, and the like. Such ingredients may be added to the present invention which would serve as a composition base and by the nature of its properties further enhance the effectiveness of the other ingredients.

Many other ingredients may be added to the above described composition without hindering it's properties for the prevention of sunburns, windburns, chapped skin, and the like. Such ingredients would include but not be limited to sunscreen agents such as PABA and zinc oxide, skin softening agents, tanning agents, skin darkening compounds, and any other desired additives, fillers, binders, extenders, and the like.

It is clear that many other ingredients may be added to the present invention without detracting from the intent of the present invention as a composition for the alleviation of pain due to burns and abrasions, ie, an analgesic. Such additional ingredients would include other analgesics, anaesthetics, antibiotics, and any other desired active ingredients, in addition to fillers, extenders, preservatives, binders, dyes, perfumes, colorants, emulsifiers, surfactants, and the like. Such ingredients may be added to the present invention which would serve to further enhance the effectiveness of the present invention.

It is clear that many other ingredients may be added to the present invention without detracting from the intent of the present invention as a composition for the treatment of chapped skin and skin abrasions. Such additional ingredients would include lanolin, aloe vera products, vitamins, zinc oxide, anaesthetics, antibiotics, analgesics, and any other desired active ingredients, fillers, extenders, preservatives, binders, dyes, perfumes, colorants, emulsifiers, surfactants, and the like. Such ingredients may be added to the present invention which would serve as a composition base and by the nature of its properties further enhance the effectiveness of the other ingredients.

It is clear that many other ingredients may be added to the present invention without detracting from the intent of the present invention as a novel composition for use as an improved protective skin barrier against bodily fluids, and other agents of irritation. Such ingredients may be added to the present invention which would serve as a composition base and by the nature of its properties further enhance the effectiveness of the other ingredients.

Having now fully described the invention, it will be apparent to one of ordinary skill in the art that many changes and modifications can be made thereto without departing from the spirit of the invention as set forth herein.

What is claimed as new and so intended to be secured by letters patent is:

1. A composition base for topical application to the skin and mucous membranes of animals including man comprising a fresh beeswax, oil, and water, wherein the ratio of beeswax to oil to water is 1:1/10:0 to 1:20:20, by volume.

2. The composition of claim 1 wherein the ratio of beeswax to oil to water is 1:1:0 to 1:6:6, by volume.

3. The composition of claim 1, wherein the ratio of beeswax to oil is 1:1/10 to 1:10, by volume.

4. The composition of claim 1 wherein the ratio of beeswax to oil is 1:1, by volume.

5. The composition of claim 1, wherein the ratio of fresh beeswax to commercial beeswaxes is 1:2 to 1:0, by volume.

6. The composition of claim 1, wherein the ratio of fresh beeswax to commercial beeswaxes is at least 1:1, by volume.

7. The composition of claim 1, wherein fresh beeswax comprises substantially all of the beeswax in the composition.

8. The composition of claim 1, wherein the beeswax is prepared from cappings.

9. The composition of claim 1, wherein fresh beeswax and consists essentially a single plant source beeswax.

10. A method for softening and moisturizing skin which comprises the steps of topically applying an effective amount of the composition of claim 1 to the skin.

11. A method for reducing wrinkling in the skin which comprises the steps of topically applying an anti-wrinklinq effective amount of the composition of claim 1 to the skin.

12. A method for treating burns which comprises the steps of topically applying a therapeutically effective amount of the composition of claim 1 to the affected area.

13. A method for treating sunburns and windburns which comprises the steps of topically applying a therapeutically effective amount of the composition of claim 1 to the affected area.

14. A method for treating cuts and abrasions which comprises the steps of topically applying a therapeutically effective amount of the composition of claim 1 to the affected area.

15. A method for treating chapped skin and chafed skin which comprises the steps of topically applying a therapeutically effective amount of the composition of claim 1 to the affected area.

16. A method for preventing sunburns and windburns which comprises the steps of topically applying a sunburn and windburn preventing effective amount of the composition of claim 1 to the affected area.

17. A method for treating and alleviating pain in the skin surface and underlying tissues which comprises the steps of topically applying an anti-pain effective amount of the composition of claim 1 to the affected area.

18. A method for providing a protective barrier against bodily fluids and other agents of irritation which comprises the steps of topically applying a protective barrier forming effective amount of the composition of claim 1 to the area of exposure.

19. A composition comprising a fresh beeswax, oil, and water.

20. An improved base for pharmaceutical and cosmetic preparations which comprises the composition of claim 1.

21. Edible food products prepared from fresh beeswax, oil, and water wherein the ratio of beeswax to oil to water is 1:1/10:0 to 1:20:20, by volume.

22. The edible food product of claim 21 which has a margarine-like consistency.

23. A method of treating animals including man by the method of applying the composition of claim 1 to the skin.

24. An edible product comprising a fresh beeswax.

* * * * *